United States Patent [19]

Kai

[11] Patent Number: 4,677,280

[45] Date of Patent: Jun. 30, 1987

[54] CONTACT LENS STERILIZATION DEVICE

[75] Inventor: Isao Kai, Kameoka, Japan

[73] Assignee: Omron Tateisi Electronics Co., Kyoto, Japan

[21] Appl. No.: 919,567

[22] Filed: Oct. 20, 1986

Related U.S. Application Data

[63] Continuation-in-part of Ser. No. 755,754, Jul. 17, 1985, abandoned.

[30] Foreign Application Priority Data

Jul. 17, 1984 [JP] Japan .................. 59-149231
Jul. 17, 1985 [JP] Japan .................. 60-149230

[51] Int. Cl.$^4$ .............................................. H05B 3/10
[52] U.S. Cl. .................... 219/385; 422/300; 219/521; 219/504; 219/441
[58] Field of Search .............. 219/385, 386, 521, 504, 219/505, 438, 439, 441; 422/116, 38, 300, 302; 126/275 E

[56] References Cited

U.S. PATENT DOCUMENTS

| | | | |
|---|---|---|---|
| 4,044,226 | 8/1977 | Kadlecik | 219/521 |
| 4,080,167 | 3/1978 | Beers | 219/385 |
| 4,165,359 | 8/1979 | Thomas | 219/521 |
| 4,256,952 | 3/1981 | Thomas | 219/521 |
| 4,379,965 | 4/1983 | Dounce | 219/505 |
| 4,388,521 | 6/1983 | Thomas | 219/386 |
| 4,472,623 | 9/1984 | Futter | 219/505 |

*Primary Examiner*—E. A. Goldberg
*Assistant Examiner*—Teresa J. Walberg
*Attorney, Agent, or Firm*—Wegner & Bretschneider

[57] ABSTRACT

A contact lens sterilization device has a case which is generally made of synthetic resin having defined therein: a bottom chamber for receiving the heating element; a middle chamber for receiving a contact lens; a top chamber for receiving an electronic circuit for controlling the heating element therein so as to achieve a better thermal separation between the top chamber and the bottom chamber. A heating element which may be a PTC semiconductor device is secured to the lower surface of the wall separating the middle chamber and the bottom chamber by way of a heat transmission plate and secured by a holding plate and columns appending from the separation wall. The two electrodes of the heating element may be electrically in contact with the heat transmission plate and the holding plate, respectively.

14 Claims, 10 Drawing Figures

CONTACT LENS STERILIZATION DEVICE

REFERENCE TO RELATED APPLICATION

This application is a continuation-in-part of my application Ser. No. 755,754, filed July 17, 1985, now abandoned.

TECHNICAL FIELD

This invention relates to a contact lens sterilization device and in particular to a device for heating a contact lens accommodated in a case for sterilization.

PRIOR ART

As a device for sterilizing a contact lens by heating, there is known a device in which a heat transmission plate is heated by a heater so that this heat may be used to heat up a contact lens container and, once a thermostat detects that a predetermined temperature has been reached, sterilization is performed while the heat transmission plate is cooled by the ambient temperature according to a temperature drop curve determined by the heat capacity of the heat transmission plate and the heat dissipating capability of the device (U.S. Pat. No. 4,044,225). According to this device, in principle, the sterilization capability is determined by the sterilization time and the sterilization time is in turn determined by the heat capacity of the heat transmission plate.

Therefore, such a device requires a large and heavy metal plate with a sufficient heat capacity and has a tendency to be both bulky and heavy. In view of the fact that a contact lens sterilization device is a device which is used almost every day and is often necessary to be carried on a trip, it is quite inconvenient. Furthermore, the sterilization time and the sterilization temperature are significantly affected by the ambient temperature and its control is very difficult. Moreover, a thermostat may suffer from bad contact and its maintenance is troublesome.

As another contact lens sterilization device which accomplishes sterilization by heating, there is the one which is improved in that the sterilization time and the sterilization temperature are controlled according to the the heat capacity of the heat transmission plate and the ambient temperature by timer control and a contactless temperature control element (U.S. Pat. No. 4,379,965, Japanese Patent Laying-Open Publication No. 47-170256).

A more recent device utilizes a PTC (positive temperature coefficient) element, and this PTC element, received in a pocket portion of a spring biasing means, is biased and pressed against a heat conduction plate by the spring force of the spring biasing means.

However, because a PTC semiconductor chip element is as thin as 2.5 mm and receives high voltage on its both surfaces, the pocket must be extremely shallow. When a strong spring force is necessary, the metal member must have a sufficient thickness and the forming of the pocket becomes extremely difficult. And, because the spring biasing means requires a certain stroke for its spring action, the device tends to be bulky and costly. Furthermore, because the PTC semiconductor chip element easily comes off from the pocket portion, assembly work is not simple.

In order to sterilize a contact lens, it is necessary to keep the fluid temperature of the lens container at least at 80° to 90° C. over tens of minutes. Therefore, the temperature of the heat transmission plate must be raised at least to 110° C. and the heat transmission plate must have a certain size.

Additionally, in order to reduce power consumption by improving thermal efficiency, the lens container must have an enclosed structure for accommodating liquid.

Further, timer and switching elements must be provided in the container for the purpose of controlling the heating time and so on, and these are typically made of electronic component parts such as IC's and semiconductor devices for the reasons of cost and quality. Generally, the operating temperature range for semiconductor devices and other electronic component parts is from 70° to 80° C. and therefore these semiconductor devices and electronic component parts may not be provided near the heat transmission plate. Therefore, the heat transmission plate and so on must be separated from electronic components and so on in the case of the device, causing the device to be too bulky for portability and costly.

SUMMARY OF THE INVENTION

A primary object of this invention is to eliminate such problems of the prior art and to provide a contact lens sterilization device which is highly compact and lightweight.

Another object of this invention is to provide a contact lens sterilization device which is simple to assemble even when an extremely thin PTC device is used a heating element.

Yet another object of this invention is to provide a contact lens sterilization device which is compact and is yet free from the troubles arising from the transmission of heat from a heating element to an electronic circuit for controlling the heating element.

Yet another object of this invention is to provide a contact lens sterilization device which is thermally efficient and can save power consumption.

According to this invention, such objects are accomplished by providing a contact lens sterilization device, wherein a contact lens is sterilized by being heated by heat transferred from a heating element through a heat transmission plate having favorable heat conductivity, comprising: a case which is generally made of synthetic resin having defined therein: a bottom chamber for receiving the heating element therein; a middle chamber for receiving a contact lens therein; a top chamber for receiving an electronic circuit for controlling the heating element therein.

According to a certain aspect of the present invention, the lower surface of a wall separating the middle chamber and the bottom chamber being provided with a plurality of columns appended therefrom; the heating element being secured between the column by a holding plate which is secured to the bottom end of the columns. Preferably, the columns are integrally molded with the the separation wall which is in turn integrally molded with the case.

According to another aspect of the present invention, the wall separating the middle chamber and the bottom chamber comprises a heat transmission plate and the columns additionally serve as positioning members for the heat transmission plate.

According to yet another aspect of the present invention, the heat transmission plate is electrically in contact with one of two electrodes of the heating element and a lead terminal interposed between the heating element and the holding plate is in electric contact with the other electrode of the heating element.

According to this invention, because the heating element is fixedly secured to a plurality of columns made of electrically insulating material, no matter how thin the heating element chip is, no short-circuiting of the electrodes would happen and the chip is firmly secured by the columns. This is particularly advantageous when the heating element is a PTC semiconductor device. Furthermore, this is accomplished only by providing a plurality of columns in the case, the heating element may be secured without requiring any substantial space and the structure for securing it is economical for manufacture.

According to this invention, because a structure such as a spring biasing means, which is complex and expensive is not used for securing a heating element but only a plurality of of insulating columns are used for such purpose, the cost of the device may be low.

Because of the elimination of a spring biasing means which requires a certain stroke for its spring action, it now suffices if the area of the heat transmission plate and the height of the columns are needed to be secured and the device may have a very small size, making it suitable as a portable device.

Also, when the heating element is attached with a metallic spring biasing means, the heat is dissipated not only through the heat transmission plate but also through the spring biasing means and the efficiency is therefore impaired causing excessive power consumption. On the other hand, according to this invention, because only an insulating plate is placed on the side of the heating element opposite to the heat transmission plate, there is very little heat dissipation through the insulating plate and efficiency is therefore improved preventing any excessive power consumption.

Furthermore, if a conventional pocket made by deep drawing is used for securing a heating element, the distance between the electrodes effective for insulation is reduced and short-circuiting may become a problem, but, according to this invention, the heating element is supported by insulating columns and no such problem arises.

Moreover, whereas securely fixing a thin heating element with a metallic member which is highly resilient and has a shallow pocket is highly troublesome, the structure according to this invention calls only for mounting of the heating element with the columns serving as a guide therefor. Thus, the present invention provides a number of advantages such as facility of assembly, high production efficiency, and so on.

According to another aspect of this invention because a heating unit comprising the heating element and the heat transmission plate is provided in a lower part while a lens container receiving chamber above the heating unit, and an electronic circuit receiving chamber for accommodating a an electronic circuit for controlling the heating unit is located above the lens container receiving chamber, whereby the heating unit and the electronic circuit are provided in thermally separated relationship. Therefore, because the heating unit and the electronic circuit receiving device are separated from each other by the lens container receiving chamber interposed therebetween, the electronic circuit is thermally separated from the heating unit.

Furthermore, because the heating unit is provided in the lowermost part and the lens container receiving chamber is provided above the heating unit while the electronic circuit receiving chamber is provided in the uppermost part, the thermal efficiency of the heat transmission from the heating unit to the lens container is high and the electronic circuit receiving chamber separated from the heating unit is substantially free from thermal influences from the heating unit, whereby the reliability and the durability of the device may be enhanced with additional advantages of compact size and light weight for the convenience of portability. Furthermore, on account of the small size and the compact size, it has become possible to eliminate a power cord and to provide a power plug for direct connection to a power outlet.

These advantages may be achieved in a further aspect of this invention in which the heating element and the electronic control circuitry are provided in the main body of the device with the contact lens container being placed on top of the main body, either integral with the main body or being so formed that the contact lens container fits into an appropriately shaped upper surface with a cover thereover. The electronic control circuitry is located below the heating element in the main body and is separated therefrom so that the heat from the heating element does not deleteriously affect the electronic circuitry.

BRIEF DESCRIPTION OF THE DRAWINGS

Now this invention is described in the following with reference made to the appended drawings, in which:

FIG. 8 is an exploded perspective view of another embodiment of the contact lens sterilization device according to this invention.

FIG. 9 is a vertical sectional view taken along line II—II of FIG. 8 of an assembled device according to FIG. 8.

FIG. 10 is a vertical sectional view taken along line III—III of FIG. 8 of an assembled device according to FIG. 8.

DETAILED DESCRIPTION OF PREFERRED EMBODIMENTS

Figure 1:
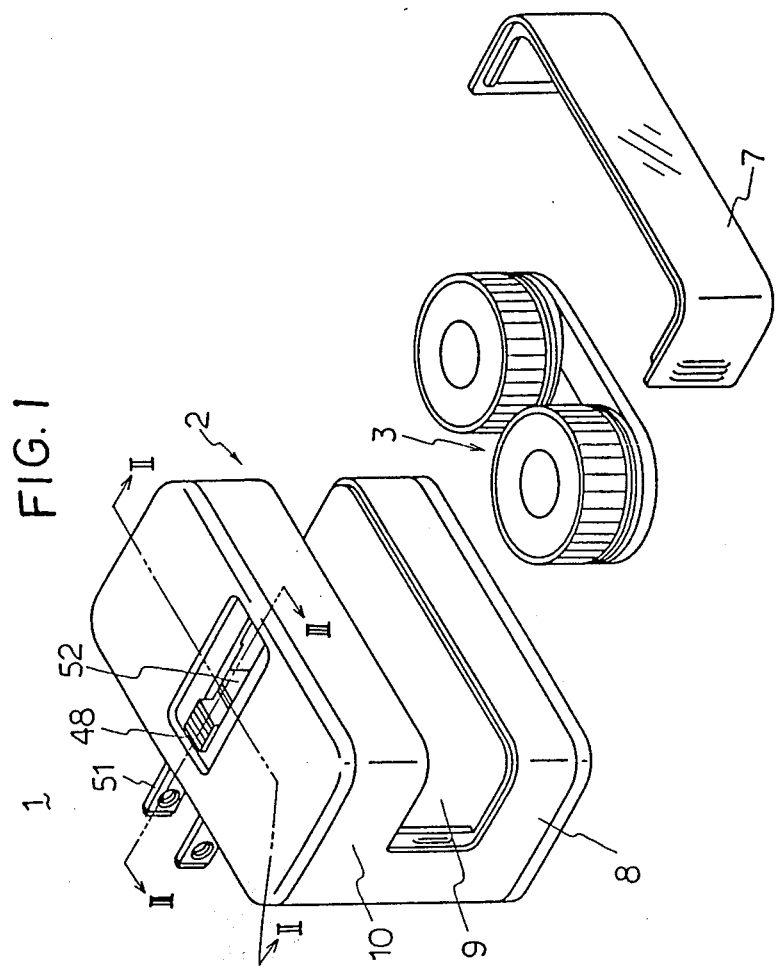
FIG. 1 is a perspective view of an embodiment of the contact lens sterilization device of this invention.
Figure 2:
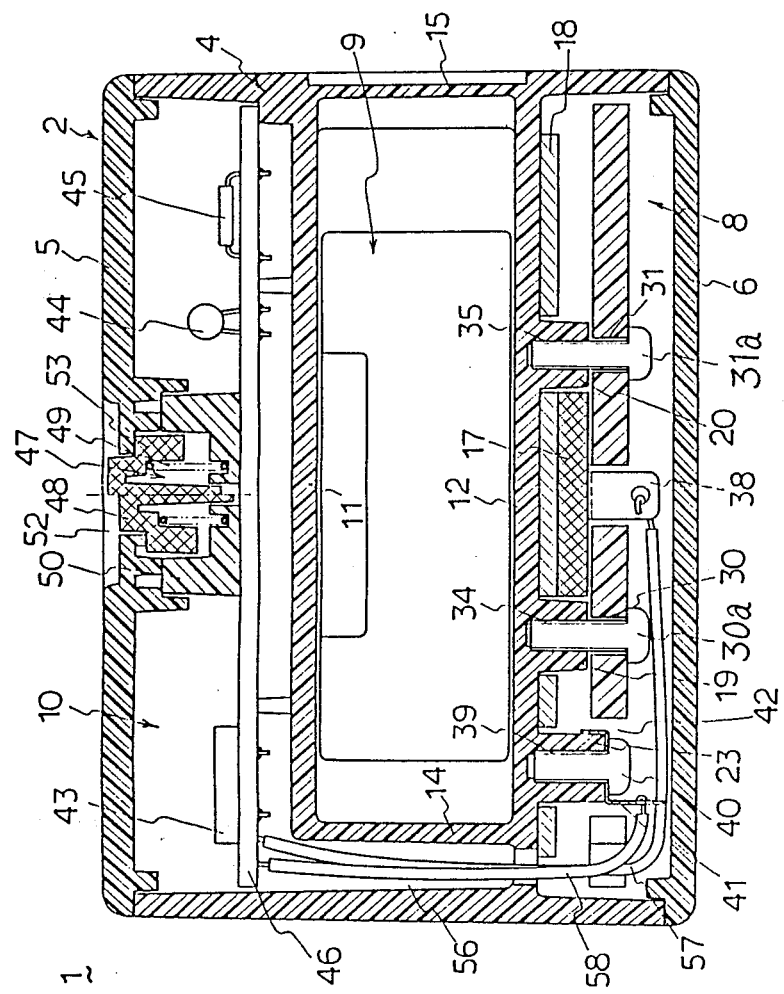
FIG. 2 is a vertical sectional view taken along line II—II of FIG. 1.
Figure 3:
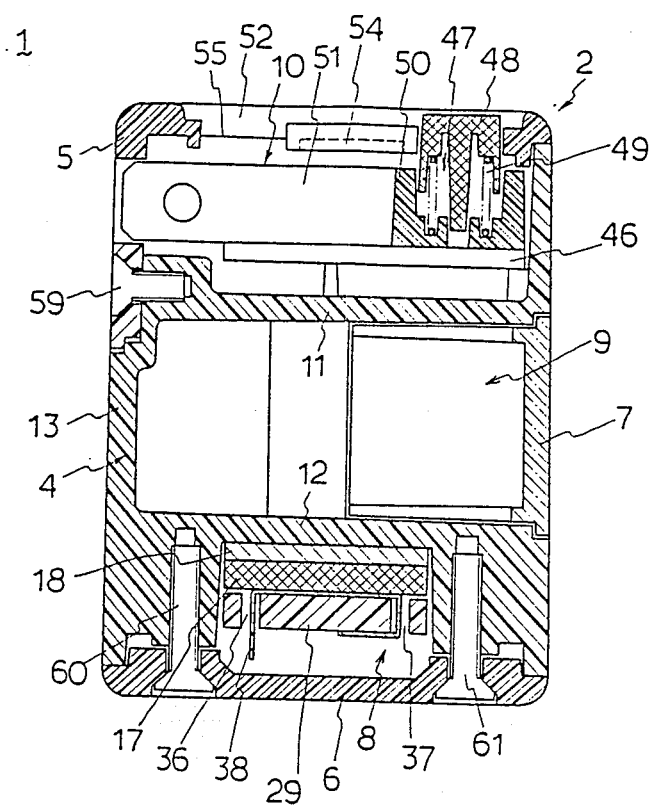
FIG. 3 is a vertical sectional view taken along line III—III of FIG. 1.

FIG. 1 is a perspective view of an embodiment of the contact lens sterilization device of this invention; FIG. 2 is a vertical sectional view taken along line II—II of FIG. 1; and FIG. 3 is a vertical sectional view taken along line III—III of FIG. 1.

The contact lens sterilization device 1 of this invention comprises a device main body 2 and a contact lens container 3. An external housing of the device main body 2 comprises a main body case 4, an upper cover 5, a bottom cover 6 and a front cover 7.

A heating chamber 8 is defined in the bottom part of the device main body 2 by the main body case 4 and the bottom cover 6. A lens container receiving chamber 9 is defined, above the beating chamber 8, by the main body case 4 and the front cover 7, while an electronic circuit receiving chamber 10 is defined, above the lens container receiving chamber 9, by the main body case 4 and the upper cover 5.

The lens container receiving chamber 9 comprises a ceiling wall 11, a bottom wall 12, a rear wall 13 and two side walls 14, 15 which are integrally formed with the main body case 4 as part thereof, and the front and part of the sides adjacent to the front are remained open. This open side receives the front cover 7 snugly in an elastic manner and the lens container 3 is received in the lens container receiving chamber 9 when sterilization by heating is to be conducted. The lens container 3, of course, accommodates a pair of contact lenses to be sterilized in its two internal chambers.

Figure 4:
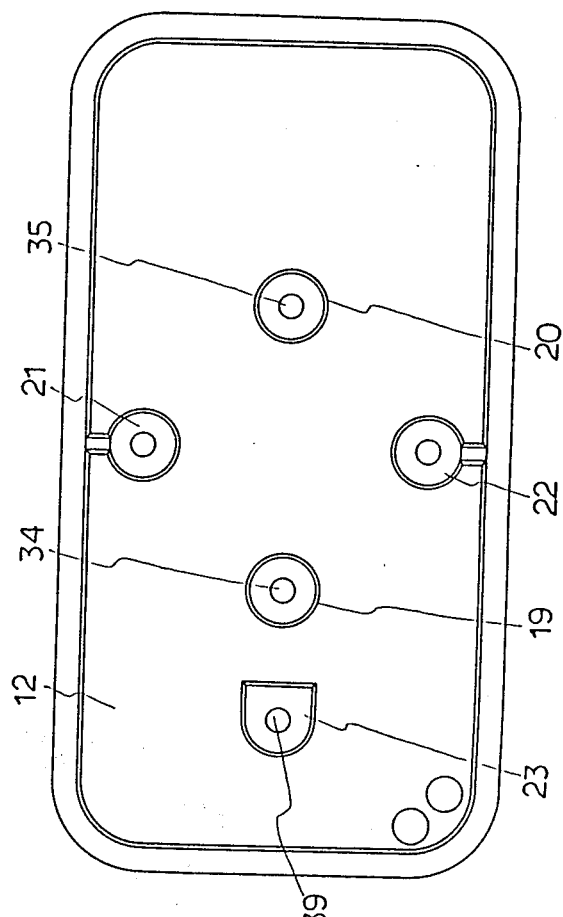
FIG. 4 is a bottom view of the main body case.
Figure 5:
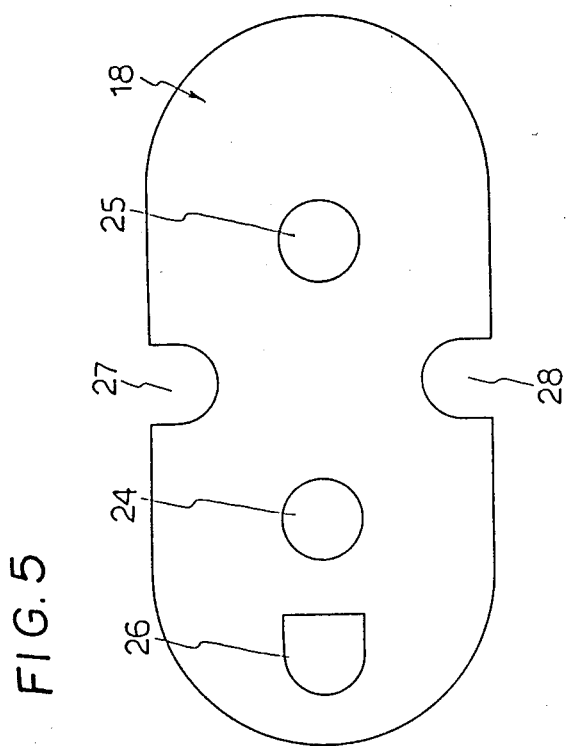
FIG. 5 is a plan view of the heat transmission plate.

The heating chamber 8 accommodates a PTC element 17 for heating and a heat transmission palate 18 made of metal. In the heating chamber 8, five columns 19, 20, 21, 22 and 23 append from the ceiling wall 12 of the heating chamber 8 (the bottom wall of the lens container receiving chamber 9) as shown in FIGS. 2 and 3 in sectional views and in FIG. 4 in a bottom view. The heat transmission plate 18 is provided with three through holes 24, 25 and 26 and two notches 27 and 28 in the portions corresponding to the columns 19 to 23 as clearly shown in FIG. 5, and the heat transmission plate 18 is positioned by the columns 10 to 23 being received in the through holes 24 to 26 and the notches 27 and 28 of the heat transmission plate 18.

Figure 6:
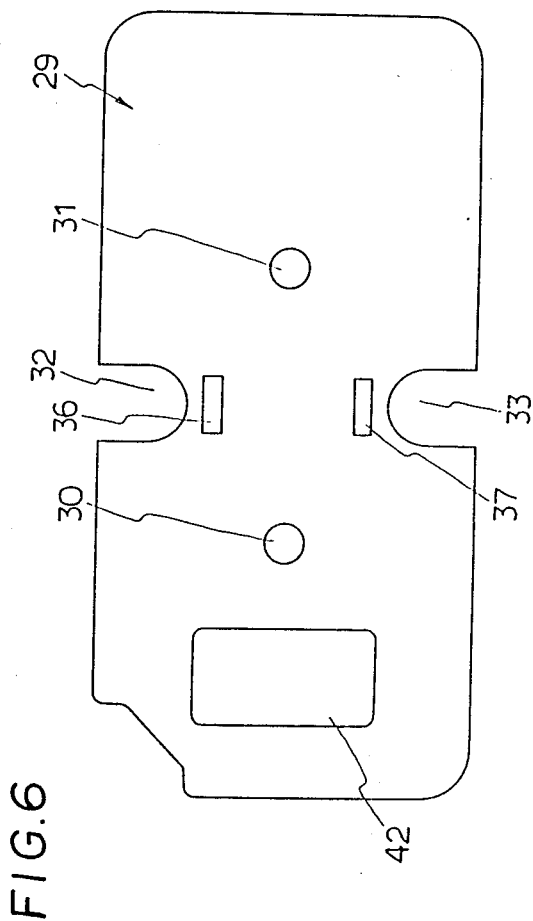
FIG. 6 is a plan view of the holding plate.

The PTC element is in the shape of a thin disc or, in other words, shaped like a coin and its one surface is closely in contact with the heat transmission plate 18 while four points around its circumference are firmly held by the four columns 19 to 22. Additionally, the PTC element 17 is supported from below by a holding plate 29 made of electrically insulating material. The holding plate 29 is provided with through holes 30 and 31 and notches 32 and 33 as clearly shown in FIG. 6 so that it may be fixed by screws 30a and 31a which are passed through the through holes 30 and 31 and received by threaded holes 34 and 35 provided in the columns 19 and 20. Furthermore, the holding plate 17 is provided with holes 36 and 37 for fitting a lead terminal 38 therein in such a manner that when the holding plate 29 is securely attached over the PTC element 17 the lead terminal 38 is in contact with one of two electrodes of the PTC element 17.

The column 23 is provided with a threaded hole 39 for securing a lead terminal 41 thereto with a screw 40. This lead terminal 41 comes in electric contact with the heat transmission plate 18 when secured with the screw 40. A rectangular hole 42 provided in the holding plate 29 is for passing a lead wire for the lead terminal 41 therethrough.

The electronic circuit receiving chamber 10 accommodates a power plug 47 and an electronic circuit board 46 carrying an IC 43 for a timer and on-off switches and other electronic component parts 44 and 45 for controlling the sterilization time.

The power plug 47 comprises a knob 48, a plug base 50 receiving the knob 48 therein, a coil spring 49 biasing the knob 48 upwardly and a plug fitting 51 securely attached to the plug base 50, and the plug fitting 51 is retractable into the device main body 2 for storage therein. Specifically, the upper cover 5 is provided with a slot 52 for guiding the knob 48 along the path of the retracting motion thereof. With reference made to FIG. 3, when the knob 48 is pushed down against the biasing force of the coil spring 49 and is moved leftwards in the sense of the drawing or, in other words, along the path of the retracting motion thereof, a step 53 formed on one side of the knob 48 slides along the lower surface of a thickened portion 54 of the upper cover 5 until the step 53 snugly engage with a thinned portion 55 of the upper cover 5. In this state, the plug fitting 51 protrude sideways from the device main body 2 so that it may be inserted into a power outlet.

A communication hole 56 is provided in the area where the rear wall 13 and the side wall 14 of the lens container receiving chamber 9 adjoin, for communication between the electronic circuit receiving chamber 10 and the heating chamber 8. Using this communication hole 56 as a guide, a pair of lead wires 57 and 58 are connected between the electronic circuit board 46 and and the lead terminals 38 and 41 through the communication hole 56 so that voltage may be applied across the two electrodes of the PTC element 17.

Thus, the heating chamber 8 and the electronic circuit receiving chamber 10 are separated by the lens container receiving chamber 9 and are thermally separated.

Now a manner in which the contact lens sterilization device of the above-described embodiment, in particular its heating chamber 8, may be assembled is described in the following.

First of all, the main body case 4 is flipped over so that the columns 19 to 23 appended from the ceiling wall 12 of the heating chamber 8 may be directed upwards. Then, the PTC element 17 is pushed into the space surrounded by the columns 19 to 22 so that the PTC element 17 may be held between them. The lead terminal 41 is mounted on the column 23 with the screw 40 so as to cause a favorable contact between the lead terminal 41 and the heat transmission plate 13. The holding plate 29 is then placed over the PTC element 17 and secured to the columns 19 and 20 by fastening the screws 30a and 31a. Finally, the bottom cover 6 is attached to the main body case 1 with screws 60 and 61. This completes the assembly of the heating chamber 8.

When a contact lens is to be sterilized with this embodiment of the contact lens sterilization device, a pair of contact lenses are placed into the lens container 3 along with suitable liquid such as pure water, salt water, sterilization liquid or detergent as required and the lens container 3 is placed into the lens container receiving chamber 9 before the lens container receiving chamber 9 is closed by the front cover 7. The plug fitting 51 of the power plug 47 is projected from the electronic circuit receiving chamber 10 and is inserted into a power outlet in the room.

Thereby, AC voltage is applied to the two electrodes of the PTC element 17 in the heating chamber 8 and the PTC element 17 is heated up. The heat from the PTC element 17 is applied to the lens container 3 in the lens container receiving chamber 9 through the heat transmission plate 18 and heats up and sterilizes the lenses in the lens container 3. The heating is continued from the time the power is turned on until the timer in the electronic circuit receiving chamber 10 runs out and the power is turned off.

Figure 7:
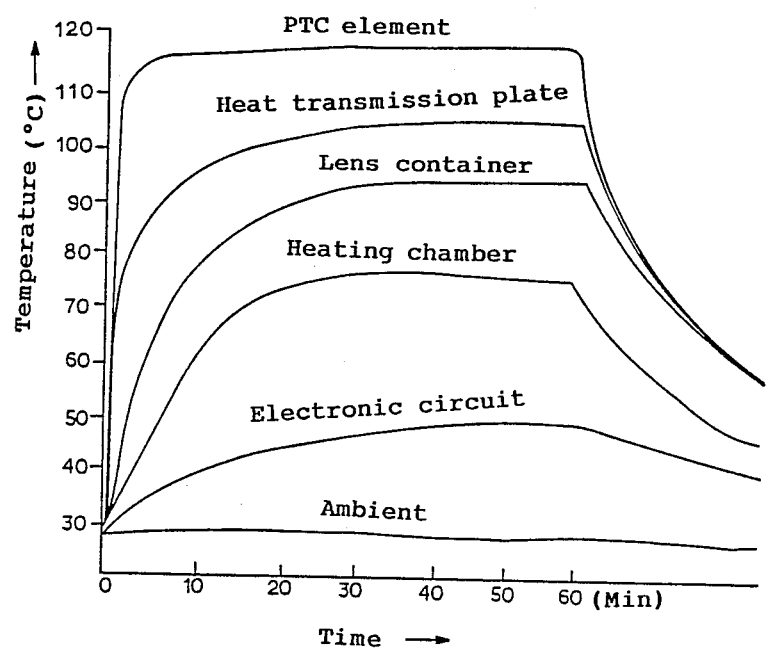
FIG. 7 is a graph showing the changes in the temperatures of various parts of the device of this embodiment after the heating is started.

FIG. 7 shows the changes in the temperatures of various parts of the device of this embodiment after the heating is started. As can be seen from this graph, as the temperature of the PTC element rises, while the temperatures of the heat transmission plate 12 and the lens container 3 rise rather sharply, the temperature of the electronic circuit rise only much more slowly and gradually without reaching a high temperature when the sterilization is completed.

The temperature of the heating chamber 8 is 70° to 80° C. and is approximately 50° C. higher than the ambient temperature. Therefore, electronic component parts can not be placed in the heating chamber 8. However, the temperature of the electronic circuit receiving chamber 10, separated from the heating chamber 8, is only 50° C. and only 20° C. higher than the ambient temperature. Therefore, the electronic component parts such as IC's in the electronic circuit receiving chamber 10 are not affected by the temperature.

FIGS. 8–10 depict another aspect of this invention, in which the electronic control circuitry and the heating element are arranged in the main body, with the heating element above and separated from the circuitry. FIG. 8 shows main body 103 with an integral plug and an upper surface shaped so as to receive contact lens holder 102 and cover 101. It is possible, but not preferred, for the holder 102 to be formed integrally with the main body 103, but this arrangement has the disadvantage of being difficult to clean while avoiding water damage to the circuitry.

FIG. 9 and 10 show this embodiment in sectional view. The component parts are essentially analogous to the parts shown in FIGS. 2 and 3. Contact lens container 104 is shown as having two chambers 105 and 105', disposed above heating element chamber 106. PTC element 107, which is of the same structure as the heating element in the other preferred embodiment of this invention, is situated in the top of heating element chamber 106 and as such is separated by an air gap or the like from electronic circuit receiving chamber 109. Heat transmission plate 108 serves to transmit heat from PTC element 107 to the lens container 104. The electronic circuitry 112, to which plug fitting 110 is affixed, are like the circuits disclosed in the other embodiment of this invention and will not be described further to avoid repetition. The lower portion of heating element chamber 106 is separated from the electronic circuitry chamber 109 by gap 111, which serves to protect the circuitry from excessive heat. The heating element chamber 106 has a bottom plate 116 and the electronic circuitry chamber 109 has a top plate 115 which form gap 111 therebetween. The gap 111 can be formed by columns 113 and 114 which can be integrally molded with the case and act to align the parts of the main body disclosed in this embodiment of the invention as explained in connection with the first preferred embodiment of this invention above.

Although the present invention has been shown and described with reference to the preferred embodiment thereof, and in terms of the illustrative drawings, it should not be considered as limited thereby. Various possible modifications and alterations could be conceived of by one skilled in the art to any particular embodiment, without departing from the scope of the invention. Therefore it is desired that the scope of the present invention should be defined not by any of the perhaps purely fortuitous details of the shown preferred embodiment, or of the drawings, but solely by the scope of the appended claims, which follow.

What we claim is:

1. A contact lens sterilization device, wherein a contact lens is sterilized by being heated by heat transferred from a heating element through a heat transmission plate having favorable heat conductivity, comprising:

a main body, a contact lens container and a cover adapted to fit onto the top of the main body, holding therein the contact lens container, the main body having a top surface shaped to receive the contact lens container and comprising a bottom chamber for receiving an electronic circuit for controlling the heating element and a top chamber for receiving the heating element therein.

2. A contact lens sterilization device as defined in claim 1, wherein the top and bottom chambers are separated by a gap sufficient to protect the electronic circuitry from the deleterious effects of heat from the heating element.

3. A contact lens sterilization device as defined in claim 2, wherein the top chamber has a bottom plate and the bottom chamber has a top plate which is separated from the bottom plate to form the gap sufficient to protect the electronic circuitry from the deleterious effects of heat from the heating element.

4. A contact lens sterilization device as defined in claim 3, wherein the gap is formed by one or more columns formed between the bottom plate of the top chamber and the top plate of the bottom chamber.

5. A contact lens sterilization device as defined in claim 1, wherein the main body has a top surface shaped to receive the contact lens chamber.

6. A contact lens sterilization device, wherein a contact lens is sterilized by being heated by heat transferred from a heating element through a heat transmission plate having favorable heat conductivity, comprising:

a case which is generally made of synthetic resin having defined therein:

a bottom chamber for receiving the heating element therein;

a middle chamber for receiving a contact lens therein;

a top chamber for receiving an electronic circuit for controlling the heating element in the bottom chamber.

7. A contact lens sterilization device as defined in claim 6, wherein a lower surface of a wall separating the middle chamber and the bottom chamber is provided with a plurality of columns appended therefrom and the heating element is secured between the columns by a holding plate which is secured to a bottom end of the columns.

8. A contact lens sterilization device as defined in claim 7, wherein the columns are integrally molded with the separation wall which is in turn integrally molded with the case.

9. A contact lens sterilization device as defined in claim 8, wherein the wall separating the middle chamber and the bottom chamber comprises a heat transmission plate and the columns additionally serve as positioning members for the heat transmission plate.

10. A contact lens sterilization device as defined in claim 9, wherein the heat transmission plate is electrically in contact with one of two electrodes of the heating element and a lead terminal interposed between the heating element and the holding plate is in electric contact with the other electrode of the heating element.

11. A contact lens sterilization device as defined in claim 10, wherein the heating element is a PTC semiconductor device.

12. A contact lens sterilization device as defined in claim 11, wherein a pair of lead wires connected to the heat transmission plate and the holding plate, respectively, are passed through a communication passage defined in the case between the bottom chamber and the top chamber and connected to the electronic circuit received in the top chamber.

13. A contact lens sterilization device as defined in claim 12, wherein the top chamber accommodates a retractable power plug.

14. A contact lens sterilization device as defined in claim 13, wherein the middle chamber has a opening in at least one side thereof which may be closed with a cover whereby a contact lens container may be placed into the middle chamber through the opening for sterilization in enclosed condition.

* * * * *